(12) United States Patent
Procopiou

(10) Patent No.: US 6,911,560 B2
(45) Date of Patent: Jun. 28, 2005

(54) PROCESS FOR PREPARING SALMETEROL

(75) Inventor: Panayiotis Alexandrou Procopiou, Stevenage (GB)

(73) Assignee: SmithKline Beecham Corporation, Philadelphia, PA (US)

(*) Notice: Subject to any disclaimer, the term of this patent is extended or adjusted under 35 U.S.C. 154(b) by 258 days.

(21) Appl. No.: 10/297,130
(22) PCT Filed: Jun. 13, 2001
(86) PCT No.: PCT/GB01/02624
§ 371 (c)(1), (2), (4) Date: Dec. 3, 2002
(87) PCT Pub. No.: WO01/96278
PCT Pub. Date: Dec. 20, 2001

(65) Prior Publication Data
US 2003/0162840 A1 Aug. 28, 2003

(51) Int. Cl.$^7$ .............................................. C07C 213/08
(52) U.S. Cl. ........................................ 564/346; 564/346
(58) Field of Search ......................................... 564/346

(56) References Cited
FOREIGN PATENT DOCUMENTS

| EP | 0422889 | 4/1991 |
|----|---------|--------|
| EP | 0460924 | 4/1991 |
| GB | 2140800 | 12/1984 |

OTHER PUBLICATIONS

Hett, R., et. al., "Enantioselective Synthesis of Salmeterol via Asymmetric Borane Reduction", 1994, pp. 9375–9378.

Primary Examiner—Samuel Bart
Assistant Examiner—Lansana Nyalley
(74) Attorney, Agent, or Firm—Robert J. Smith

(57) ABSTRACT

Accordingly, the present invention provides a process for the preparation of a compound of formula (I) or a single enantiomer thereof, or a salt or a solvate thereof, wherein W is a chiral auxilary or hydrogen and $P^1$ and $P^2$ are each independently selected from hydrogen or a protecting group, which comprises: a) treatment of a compound of formula (II), or a salt or a solvate thereof, wherein W is a chiral auxilary and $P^3$ and $P^4$ are each independently selected from hydrogen or a protecting group, with a compound formula (III); b) treatment of the resulting product with a reducing agent; c) if required, deprotection to yield the compound of formula (I), or a salt or solvate thereof. In particular there is provided a process for producing a substantially pure single enantiomer of salmeterol 10 Claims, No Drawings

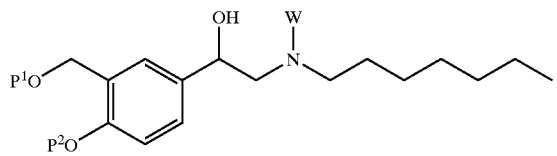

(I)

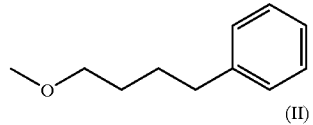

(II)

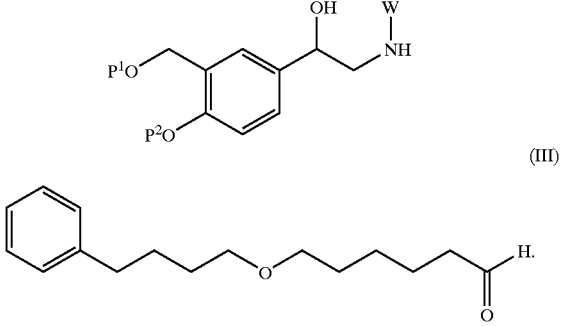

(III)

PROCESS FOR PREPARING SALMETEROL

This application is filed under 35 U.S.C. §371 as the United States National Phase Application of International Application No. PCT/GB01/02624 filed Jun. 13, 2001 claiming priority from GB Application No. 0014546.6 filed Jun. 14, 2000, the disclosures of which are incorporated herein by reference in their entirety.

This invention relates to a process for the preparation of salmeterol and to intermediates in the process.

Processes for preparing salmeterol either as a racemate or in enantiomerically pure form have been described in GB 2140 800 and EP 0422 889.

EP 0460924 discloses the compound (R)-(−)-4-amino-3,5-dichloro-α[[[6-[2-(2-pyridinyl)ethoxy]hexyl]amino]methyl]benzenemethanol and processes for its preparation employing chiral auxiliaries.

Methods of preparing a substantially pure single enantiomer often involve the resolution of diastereoisomers. However where one enantiomer is preferred this process is wasteful unless the unwanted enantiomer can be recycled. It is preferable to be able to efficiently synthesise directly one enantiomer in a substantially pure form.

The present invention relates to a new process for the preparation of salmeterol especially as a single enantiomer, which may result in time and/or cost savings and the enantiomeric excess may be superior to that previously obtainable.

Accordingly, the present invention provides a process for the preparation of a compound of formula (I)

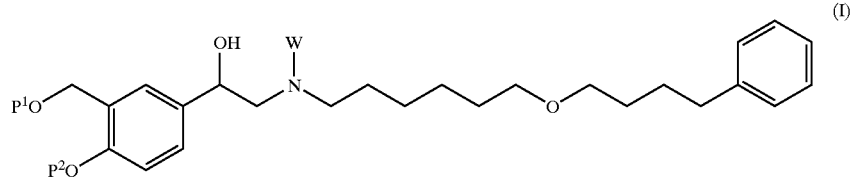

or a single enantiomer thereof, or a salt or a solvate thereof, wherein W is a chiral auxiliary or hydrogen and $P^1$ and $P^2$ are each independently selected from hydrogen or a protecting group, which comprises:

a) treatment of a compound of formula (II),

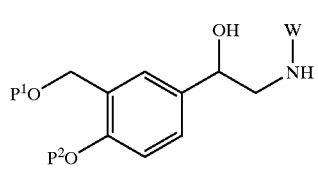

or a salt or a solvate thereof, wherein W is a chiral auxiliary and $P^1$ and $P^2$ are as defined above, with a compound of formula (III),

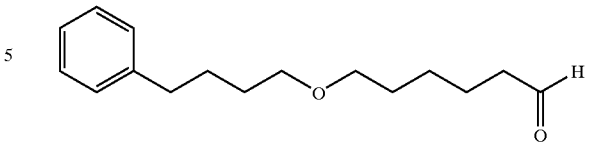

b) treatment of the resulting product with a reducing agent,
c) if required, deprotection to yield the compound of formula (I),
or a salt or solvate thereof.

This process uses a commercially well established intermediate (referred to as compound of formula (V) below) known in the synthesis of salmeterol in a simple and robust process that may be used on a commercial scale the process uses relatively mild reagents with minimal toxicity that are readily available and inexpensive and does not require the use of sensitive or expensive catalysts that may be environmentally damaging especially when used on a large scale. Furthermore the yield of the process means the chiral synthesis of salmeterol using this process is now commercially viable.

Advantageously the process is very clean, avoiding the formation of undesirable biproducts, such as caused by esterification of the unprotected hydroxyl β to the nitrogen including the hydroxyl in the chiral auxiliary, which reduces the amount of purification necessary for the final product which may result in cost savings. Such esterification by-products have surprisingly been found to be a particular problem with use of analogous compounds of formula (III) represented by the formula (IIIa)

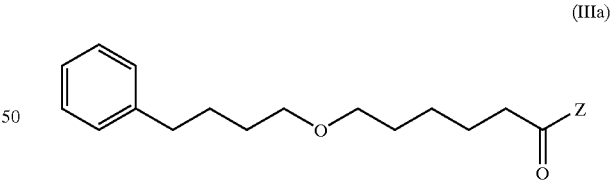

wherein Z represents halogen, hydroxyl or together with the carbonyl represents an activated ester. The problem is particularly evident wherein Z represents halogen.

Additionally since the process does not require the hydroxyl β to the nitrogen to be protected (e.g. with a protecting group as such, or else masked as a carbonyl), it avoids the unnecessary use of unpleasant reducing agents (e.g. diborane) at a late stage in the process and/or expensive catalysts or protecting reagents.

Furthermore maintaining the presence of the chiral auxiliary in the compound of formula (II) during the coupling between the compound of formula (II) and the compound of formula (III) ensures that only the desired product is obtained because the chiral auxiliary acts as a protecting group in this reaction.

In one or more of these respects the process is advantageous over processes described in the prior art, such as EP 460924.

The process also provides an efficient way of producing a substantially pure single enantiomer of salmeterol.

Thus a suitable process for the preparation of the compound of formula (Ia)

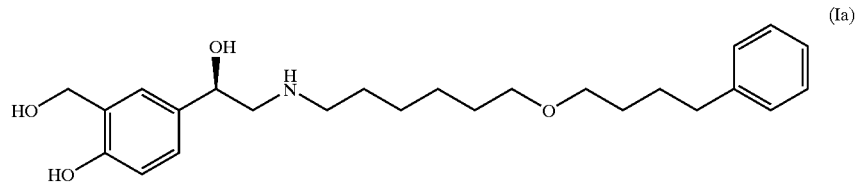
(Ia)

(R-salmeterol) or a salt or a solvate thereof, comprises:
a) treatment of a compound of formula (II¹),

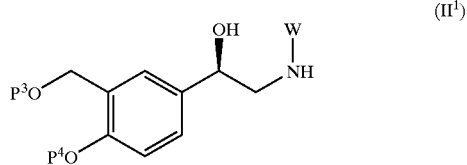
(II¹)

or a salt or a solvate thereof, wherein W is a chiral auxiliary and $P^3$ and $P^4$ independently represent a protecting group, with a compound of formula (III) as defined above
b) treatment of the resulting product with a reducing agent,
c) if required, deprotection to yield the compound of formula (Ia),
d) optional conversion to a corresponding salt or solvate thereof.

An analogous process may be used to prepare S-salmeterol by selecting a suitable chiral auxiliary.

Preferably W represents a chiral auxiliary, more preferably W represents a moiety of formula (Y)

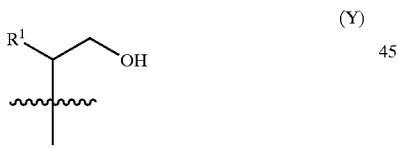
(Y)

or a single enantiomer thereof, wherein $R^1$ represents $C_{1-6}$alkyl e.g. iso-propyl, iso-butyl or sec-butyl or optionally substituted phenyl or benzyl wherein the optional substitution is one or more independently selected from $C_{1-6}$alkyl, halogen, hydroxy, $C_{1-6}$alkoxy or nitro e.g. para-hydroxyphenyl.

More preferably W may represent $Y^1$

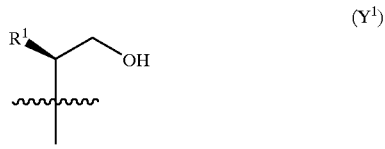
(Y¹)

wherein $R^1$ is as defined above. Alternatively it represents a moiety of formula (Y²)

(Y²)

wherein $R^1$ is as defined above, especially a moiety of formula (Y²).

Preferably $R^1$ represents phenyl optionally substituted as described above, iso-propyl or sec-butyl.

In an especially preferred aspect of the invention W represents a moiety of formula (Ya),

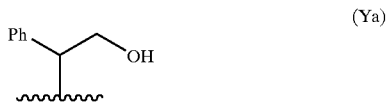
(Ya)

most preferably the moiety of formula (Ya¹),

(Ya¹)

and/or the moiety of formula (Ya²),

(Ya²)

Preferably in the reaction between compounds of formula (II) with compounds of formula (III) $P^1$ and $P^2$ will independently represent a protecting group.

Preferably $P^1$ and $P^2$ together with the oxygens to which they are attached to represent acetonide. Preferably $P^3$ and $P^4$ together with the oxygens to which they are attached to represent acetonide.

The salt that is most preferred is the xinafoate salt.

Particularly preferred aspects of the invention include those in which each variable in the compounds of formulae (I), (II) and (III) is selected from the preferred groups for each variable. Even more preferable aspects of the invention include those in which each variable in the compounds of formulae (I), (II) and (III) is selected from the more preferred or most preferred groups for each variable.

"Protecting group" is a term well understood by persons skilled in the art. Protecting groups may be any conventional protecting groups, for example as described in "Protective Groups in Organic Synthesis" by Theodora Greene and Peter G. M. Wuts (John Wiley and Sons Inc. 1999).

$P^1$ and $P^2$ may be an entity with the capacity to protect two alcohols simultaneously for example, where $P^1$ and $P^2$ taken together with the oxygens to which they are attached represent an acetal or ketal e.g. acetonide. Alternatively $P^1$ and $P^2$ could be separate or different protecting groups.

Hydroxyl protecting groups $P^1$ and $P^2$ include but are not limited to carboxylic acid esters e.g. acetate ester, aryl esters e.g. benzoate ester, acetals/ketals e.g. acetonide and benzylidene, ethers e.g. O-benzyl and p-methoxybenzyl ether, tetrahydropyranyl ether and silyl ethers e.g. tert-butyldimethylsilyl ether.

Protecting groups can be removed by acid or base catalysed hydrolysis or reduction for example hydrogenation. Silyl ethers may require hydrogen fluoride or tetrabutylammonium fluoride to be cleaved.

A "chiral auxiliary" is a moiety that is introduced into a molecule to influence the stereochemistry of the product formed, and is removed in whole or part at a later time. A chiral auxiliary may simultaneously function as a protecting group.

The chiral auxiliary in this process will typically be removed by hydrogenolysis using for example a palladium on carbon catalyst or preferably using palladium hydroxide (Pearlman's catalyst). Advantageously when Pearlman's catalyst is used the removal of the chiral auxiliary is most efficient. This method of removal is especially suitable where $R^1$ is phenyl or a substituted phenyl. Alternatively the nitrogen, to which the moiety of formula (Y) is attached, may be derivatised under oxidising conditions to form the N-oxide before elimination by heating to give a secondary amine.

Many chiral auxiliaries are commercially available, and persons skilled in the art would choose one based on the properties desired i.e. the absolute stereochemistry desired and compatibility with the processes being used. Chiral auxiliaries suitable for use in this process include but are not limited to the S-isomer and/or the R-isomer of phenyl glycinol and substituted derivatives thereof, valinol, isoleucinol, leucinol and phenyl alaninol.

To induce the stereochemistry required for the preparation of R-salmeterol (compound of formula (Ia)) it is usually necessary to use the S-isomer of the chiral auxiliary and conversely, to prepare S-salmeterol the R-isomer of chiral auxiliary should usually be used. Therefore where the compounds of formulae (I) and (II) have two chiral centres they will not generally be both S or both R, they may be for example R,S; in this situation the opposite enantiomer will be S,R.

However more important than what is the designation of the chiral centre of the chiral auxiliary, is that the hydroxy and nitrogen (attached to carbons 1 and 2 respectively as designated in the compound of formula (II$^x$))

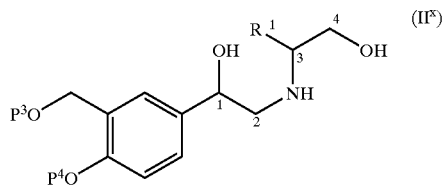

are syn with respect to each other wherein $P^3$ and $P^4$ are as defined above.

It will be clear to a person skilled in the art that a compound of formula (II$^x$) is free to rotate about the carbon numbered 2 above. It is hypothesised that this rotation can be minimised by the addition of an inert metal salt such as calcium chloride.

Presumably when the rotation is restricted as described above and carbon 1 is a carbonyl, $R^1$ blocks the approach of the hydride on one face of the said carbonyl and any hydride can only approach from the other face. The alcohol produced by such a reduction is in close proximity to $R^1$ in the area previously not available for the hydrides approach. Thus the stereochemistry induced can be influenced by chosing the spatial arrangement of the group $R^1$.

The term "reducing agent" is a term well understood by persons skilled in the art and can include hydride sources like borohydrides and alkali metal borohydrides, but would also include hydrogen in catalytic hydrogenation wherein a suitable catalyst such as palladium on carbon may be used.

Other suitable hydride sources include sodium triacetoxyborohydride, tetrabutylammonium triacetoxyborohydride, sodium cyanoborohydride, polymer bound borohydride or sodium borohydride in a solvent such as acetic acid wherein triacetoxyborohydride is formed in situ, diborane or a complex metal hydride.

For part b) of the process the reducing agent may be present concomitant with the compounds of formula (II) and (III) for example where the reducing agent is triacetoxyborohydride, and in other circumstances it is necessary to wait until the reaction between compounds of formula (II) and (III) is complete before the reducing agent is introduced, for example where the reducing agent is an alkali metal borohydride or hydrogen.

Preferably the reducing agent will be present concomitant with the compounds of formula (II) and (III) since "one pot" reactions are advantageous in a large scale manufacturing process.

Compounds of formula (II) may be reacted with compounds of formula (III) by stirring them together at non-extreme temperatures, for example −10 to 60° C., especially 10 to 60° C., for example ambient temperature, in an inert solvent such as dichloromethane (DCM) possibly in the presence of a water scavenger for example molecular sieves, magnesium sulphate or triethylorthoformate.

The protecting groups and/or the chiral auxiliary may be chosen so that they are removed during a step in the process rather than requiring a separate deprotection step. This may minimise the requirements for deprotection, at the end of the process, to yield compounds of formula (I). Preferably all deprotections will be effected when the chiral auxiliary is removed. Deprotection when used in this specification may refer to or include the removal of the chiral auxiliary.

Reduction with a hydride reducing agent can be performed in an inert aprotic solvent for example DCM or tetrahydrofuran in a nitrogen atmosphere typically at non-extreme temperatures, for example −10 to 60° C., especially 10 to 60° C., particularly ambient temperature.

Compounds of formula (III) can be prepared from oxidation of 6-(4-phenybutoxy)hexyl bromide the preparation of which is described in DE 3414752.

Compounds of formula (II) defined above also form an aspect of the invention, in particular some non-limiting examples include:

1-(2,2-dimethyl-4H-1,3-benzodioxin-6-yl)-2-[(2-hydroxy-1-phenylethyl)amino]ethanol;

2-{[2-(2,2-dimethyl-4H-1,3-benzodioxin-6-yl)-2-hydroxyethyl]amino}-3-methylpentan-1-ol;

2-{[2-(2,2-dimethyl-4H-1,3benzodioxin-6-yl)-2-hydroxyethyl]amino}-3-methylbutan-1-ol;

2-{[2-(2,2-dimethyl-4H-1,3-benzodioxin-6-yl)-2-hydroxyethyl]amino}-3-phenylpropan-1-ol;

2-{[2-(2,2-dimethyl-4H-1,3-benzodioxin-6-yl)-2-hydroxyethyl]amino}-3-methylpentan-1-ol.

Also provided is a process for the preparation of compounds of formula (II) as defined above which comprises, treatment of a compound of formula (IV)

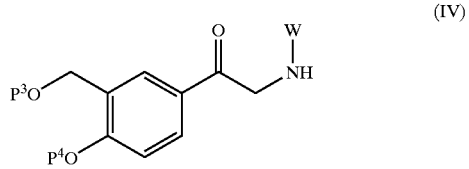

(IV)

wherein W is a chiral auxiliary and $P^3$ and $P^4$ are defined above, with a reducing agent such as a hydride source e.g. sodium borohydride. Preferably this process takes place in the presence of an inert metal salt such as calcium chloride suitably at non-extreme temperatures e.g. below ambient, such as 0° C. This allows the desired stereochemistry to be introduced efficiently with good enantiomeric excess at an early stage in the synthesis, using inexpensive and relatively harmless reagents. Furthermore the enantiomeric excess may be increased by recrystallisation of the product of this process.

Compounds of formula (IV) are novel and also form an aspect of the invention; in particular some non-limiting examples include:

1-(2,2-dimethyl-4H-1,3-benzodioxin-6-yl)-2-[(2-hydroxy-1-phenylethyl)amino]ethanone;
1-(2,2-dimethyl-4H-1,3-benzodioxin-6-yl)-2-{[1-(hydroxymethyl)-2-methylbutyl]amino}ethanone;
1-(2,2-dimethyl-4H-1,3-benzodioxin-6-yl)-2-{[1-(hydroxymethyl)-2-methylpropyl]amino}ethanone;
2-[(1-benzyl-2-hydroxyethyl)amino]-1-(2,2-dimethyl-4H-1,3-benzodioxin-6-yl)ethanone;
1-(2,2-dimethyl-4H-1,3-benzodioxin-6-yl)-2-{[1-(hydroxymethyl)-3-methylbutyl]amino}ethanone.

Compounds of formula (IVa)

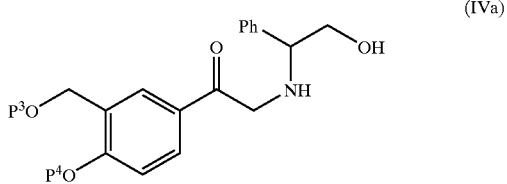

(IVa)

wherein $P^3$ and $P^4$ are as defined above, can be prepared from compounds of formula (V)

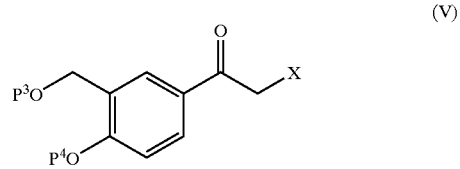

(V)

wherein X represents a leaving group e.g. halogen preferably bromine, and $P^3$ and $P^4$ are defined above, by treatment with (S)-phenylglycinol, in the presence of a non-nucleophilic base in an inert solvent at non-extreme temperatures e.g. 0 to 60° C., e.g. room temperature. Preferably $P^3$ and $P^4$ together with the oxygens to which they are attached represent acetonide during this reaction.

Preferably compounds of formula (IV) may be prepared from compound of formula (Va)

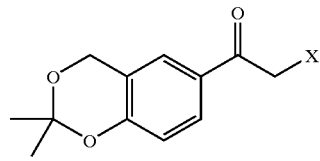

(Va)

wherein X is a leaving group for example halogen such as chloro, bromo or iodo; or compounds of formula (IV) may be prepared from compounds of formula (Vb)

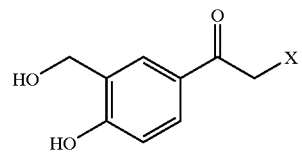

(Vb)

wherein X is a leaving group e.g. halogen.

Other compounds of formula (IV) may be prepared by analogous processes.

Most preferably compounds of formula (IV) will be prepared from compounds of (Va). Compounds of formula (Va) can be prepared from treating 2-bromo-1-(4-hydroxy-3-hydroxymethyl-phenyl)ethanone, the preparation of which is described in GB 2140 800, with 2-methoxypropene in acetone in the presence of an acid for example p-toluenesulphonic acid in a nitrogen atmosphere.

Other compounds of formula (V) can be prepared by standard methods from 2-bromo-1-(4-hydroxy-3-hydroxymethyl-phenyl)ethanone.

It will be clear to persons skilled in the art the enantiomeric excess obtained in the compound of formula (I) will depend on the enantiomeric excess of intermediate (II) which in turn is influenced by the enantiomeric excess of the chiral auxiliary. If desired, the above process may be adapted for preparation of racemic salmeterol using racemic intermediates.

Preferably, however, the process prepares one enantiomer of salmeterol suitably free of the other enantiomer e.g. in enantiomeric excess of greater than 90%, preferably greater than 95%, especially greater than 99%.

Intermediates should preferably be used in enantiomeric excess of 90%, preferably greater than 95%, especially greater than 99%.

Other aspects of this invention include the use of compounds of formula (II) and (IV) and (V) or deprotected derivatives thereof in the preparation of compounds of formula (I), salmeterol, single enantiomers thereof, or a salt or a solvate thereof.

According to another aspect of the invention, is provided a compound of the formula (IIc),

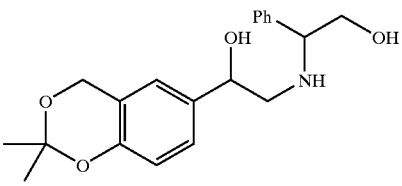

(IIc)

or a single enantiomer thereof or a salt or a solvate thereof.

Advantageously compounds of formula (IIc) are crystalline which aids purification and are therefore preferred.

According to another aspect of the invention, is provided the intermediates of the general formula (VI),

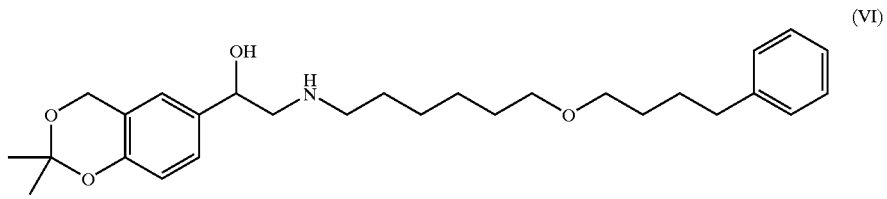

(VI)

or a salt or solvate thereof; or
an intermediate of formula (VIa)

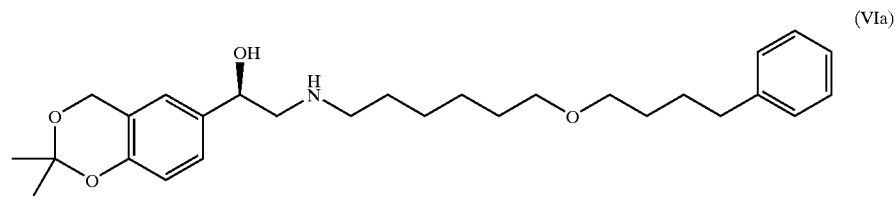

(VIa)

and/or a salt or a solvate thereof; and/or intermediate of formula (VIb)

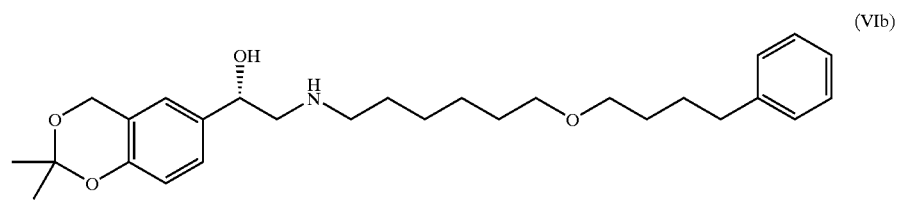

(VIb)

or a salt or a solvate thereof.

According to a further aspect of the invention, is provided an intermediate of formula (VIIa),

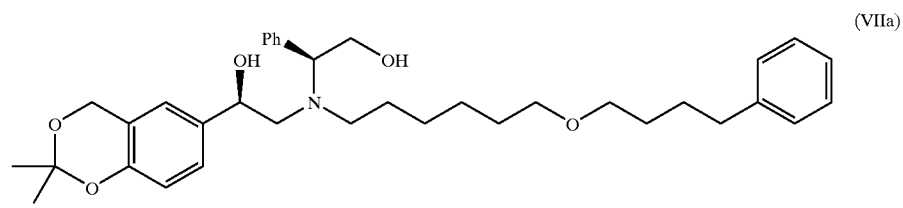

(VIIa)

and/or a salt or a solvate thereof and an intermediate of formula (VIIb)

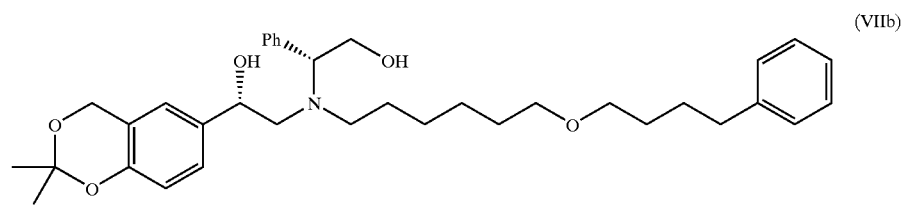

(VIIb)

or a salt or solvate thereof.

A further aspect of the invention is use of compounds of formula (II) in the preparation of compounds of formula (I), and also the use of compounds of formula (IV) and (V) in the preparation of compounds of formula (II) or salts or solvates thereof.

EXAMPLES

LCMS was conducted on an ODS2 column (5 cm×4.6 mm) eluting with 0.05% $HCO_2H$ (solvent A) and 0.05% $HCO_2H$ in acetonitrile (solvent B), using the following elution gradient 0 min 10% B, 0–12 min 90% B, 12–15 min 90% B, 15–17 min 10% B at a flow rate of 1 ml/min detecting at 230 nm. The mass spectra were recorded on a Fisons VG Platform spectrometer using electrospray positive mode (ES+ve).

1-(2,2-Dimethyl-4H-1,3-benzodioxin-6-yl)-2-{[(1S)-2-hydroxy-1-phenylethyl]amino}ethanone (S)-Phenylglycinol (28.9 g) was added in two portions to a solution of 2-bromo-1-(2,2-dimethyl-4H-1,3-benzodioxin-6-yl)ethanone (40 g) and N,N-di-iso-propylethylamine (48.9 ml) in THF (500 ml) under nitrogen. After 4 h the resulting white precipitate was removed by filtration and the mother liquor concentrated in vacuo to give an orange oil. Acetonitrile (40 ml) was added and then removed in vacuo to give a light orange solid which was pulverised and triturated with cold acetonitrile (50 ml). The resulting solid was collected by filtration and washed with acetonitrile (2×30 ml) to give the title compound (38.5 g) as a white solid.

$^1$H NMR includes δ ($CDCl_3$, 300 Mz): 1.47 (6H, s), 2.40 (1H, bs), 3.59 (1H, dd, J=11, 9 Hz), 3.70 (1H, dd, J=11, 4 Hz), 3.81 (1H, dd, J=9, 4 Hz), 3.88 (1H, d, J=18 Hz), 3.97 (1H, d, J=18 Hz), 4.77 (2H, s), 6.7–7.7 (8H, m).

(1R)-1-(2,2-Dimethyl-4H-1,3-benzodioxin-6-yl)-2-{[(1S)-2-hydroxy-1-phenylethyl]amino}ethanol To a cooled mixture (internal temp. 2° C.) of 1-(2,2-dimethyl-4H-1,3-benzodioxin-6-yl)-2-{[(1S)-2-hydroxy-1-phenylethyl]amino}ethanone (44.9 g) in methanol (450 ml) under nitrogen was added $CaCl_2.2H_2O$ (38.7 g) in one portion resulting in a slight exotherm (max temp ~12° C.). After the resulting clear solution had cooled to 0° C., sodium borohydride (10.5 g) was added in four portions over a 50 min period. After a further 2 h at this temperature the volatile material was removed in vacuo resulting in a thick white slurry, to which ethyl acetate (500 ml) was added. The mixture was filtered through a short plug of Hyflo Supercel and the filtrate was washed with water (150 ml), brine (150 ml), dried ($Na_2SO_4$) and concentrated in vacuo to give a thick orange oil. The oil was dissolved in acetonitrile (150 ml) and cooled to 5° C. for 18 h. The resulting crystals were filtered and washed with acetonitrile (3×30 ml) to give the title compound (23.9 g). The mother liquor from the filtration was concentrated in vacuo and taken up in acetonitrile (50 ml), cooled to 5° C. for 18 h to provide (after filtration and washing) a second crop of the title compound (3.4 g).

$^1$H NMR includes δ ($CDCl_3$, 300 Mz): 1.43 (6H, s), 2.55 (1H, dd, J=12, 9 Hz), 2.65 (1H, dd, J=12, 4 Hz), 2.88 (1H, bs), 3.57 (1H, dd, J=11, 9 Hz), 3.67 (1H, dd, J=11, 4 Hz), 3.73 (1H, dd, J=9, 4 Hz), 3.54 (1H, dd, J=9, 3 Hz), 4.71 (2H, s), 6.64–7.30 (8H, m).

LCMS RT=5.11 min, ES+ve 344 (MH)$^+$ $[α]_D^{20}$+43.1 (c 1.02 in $CH_2Cl_2$)

6-(4-Phenylbutoxy)hexanal

A mixture of DMSO (100 ml) and $NaHCO_3$ (14.1 g) was heated to 150° C. under nitrogen (the mixture had been thoroughly de-gassed prior to heating). 6-(4-Phenylbutoxy)hexyl bromide (10.0 g) was then added in one portion and the mixture was stirred at 150° C. for 5–6 min before it was cooled to 20° C. over a 10 min period. Diethyl ether (100 ml) was added, followed by water (100 ml). The layers were separated and the aqueous layer extracted with diethyl ether (200 ml). The combined organic layers were washed with water (2×100 ml), dried ($MgSO_4$) and concentrated in vacuo to give the title compound (8.4 g) which was used without further purification.

LCMS RT=12.03 min, ES+ve 249 (MH)$^+$ (1R)-1-(2,2-Dimethyl-4H-1,3-benzodioxin-6-yl)-2-{[(1S)-2-hydroxy-1-phenylethyl][6-(4-phenylbutoxy)hexyl]amino}ethanol To a cloudy mixture of (1R)-1-(2,2-dimethyl-4H-1,3-benzodioxin-6-yl)-2-{[(1S)-2-hydroxy-1-phenylethyl]amino}ethanol (500 mg) and crude 6-(4-phenylbutoxy)hexanal (400 mg) in $CH_2Cl_2$ (3 ml) under nitrogen was added sodium triacetoxyborohydride (433 mg) in one portion. A gelatinous mixture formed initially which thinned over a 15 min period. The resulting light yellow solution was stirred for 18 h before it was partitioned between ethyl acetate (10 ml) and saturated aqueous $NaHCO_3$ (30 ml). The aqueous layer was extracted with ethyl acetate (3×20 ml) and the combined organic layers were dried ($MgSO_4$) and concentrated in vacuo to give the title compound (725 mg).

$^1$H NMR includes δ ($CDCl_3$, 400 Mz): 1.18–1.38 (5H, m), 1.53 (6H, s), 1.40–1.71 (9H, m), 2.33–2.41 (1H, m), 2.59–2.70 (4H, m), 2.82 (1H, dd, J=13, 5 Hz), 3.37 (2H, t, J=7 Hz), 3.41 (2H, t, J=7 Hz), 3.80 (1H, dd, J=9, 4 Hz), 3.90–4.00 (2H, m), 4.60 (1H, dd, J=9, 4 Hz), 4.83 (2H, s), 6.79 (1H, d, J=8 Hz), 6.96 (1H, d, J=2 Hz), 7.09 (1H, dd, J,=8, 2 Hz), 7.15–7.2 (3H, m), 7.21–7.37 (7H, m)

LCMS RT=7.92 min, ES+ve 576 (MH)$^+$ $[α]_D^{20}$−9.0 (c 1.6 in $CHCl_3$)

(R)-(−)-2-Hydroxymethyl-4{1-hydroxy-2-[[6-(4-phenylbutoxy)hexyl]amino]ethyl}phenol A solution of (1R)-1-(2,2-dimethyl-4H-1,3-benzodioxin-6-yl)-2-{[(1S)-2-hydroxy-1-phenylethyl][6-(4-phenylbutoxy)hexyl]amino}ethanol (110 mg), in ethanol (75 ml), was hydrogenated over Pearlman's catalyst [Pd (OH)$_2$, 60% $H_2O$, 55 mg) for 18 h. The catalyst was removed by filtration and the residue was washed with methanol. The combined filtrate and washings were concentrated and then applied to a 10 g SCX ion exchange cartridge. The cartridge was eluted with methanol (4 column volumes) and then with 10% aqueous 880 $NH_3$ in methanol (3 column volumes). The ammoniacal eluent was concentrated under reduced pressure to give the title compound (69 mg) as a colourless oil.

LCMS RT=6.27 min, ES+ve 416 (MH)$^+$.

$[α]_D^{20}$−18.5 (c 0.81 in methanol)

Chiral HPLC on chiralcel column indicated only the presence of the R enantiomer RT=9.704 min (R)-(−)-2-Hydroxymethyl-4{1-hydroxy-2-[[6-(4-phenylbutoxy)hexyl]amino]ethyl}phenol, 1-hydroxy-2-naphthalenecarboxylic Acid Salt A solution of (R)-(−)-2-hydroxymethyl-4{1-hydroxy-2-[[6-(4-phenylbutoxy)hexyl]amino]ethyl}phenol (53 mg) in methanol (2 ml) was treated with 1-hydroxy-2-naphthoic acid (24 mg). The solution was evaporated to dryness to give the title compound as a solid (77 mg)

Chiral HPLC conducted on a 25 cm×0.46 cm Sumichiral OA-4100 column, eluting with hexane-dichloromethane-ethanol-trifluoroacetic acid [240:130:30:1] at a flow rate of 1 ml/min indicated the presence of the R enantiomer (98.5%) RT=18.787 min and the S enantiomer (1.5%) RT=16.417 min. The ee=97%.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

What is claimed is:

1. A process for the preparation of a compound of formula (I),

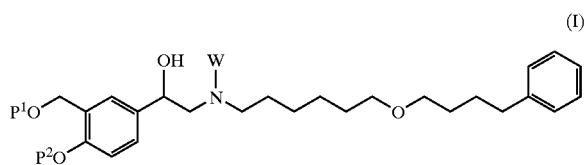

(I)

or a single enantiomer thereof, or a salt or a solvate thereof, wherein W is a chiral auxiliary or hydrogen and $P^1$ and $P^2$ are each independently chosen from hydrogen or a protecting group, which comprises a) treating a compound of formula (II),

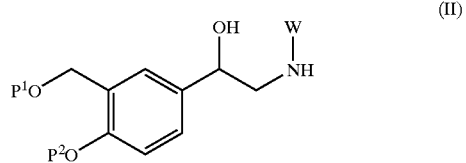

(II)

or a salt or a solvate thereof, wherein W is a chiral auxiliary and $P^1$ and $P^2$ are each independently chosen from a protecting group, with a compound of formula (III) to form a resulting product,

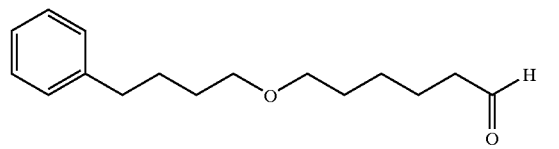

(III)

b) treating the resulting product with a reducing agent to form the compound of formula (I), or a single enantiomer thereof, or a salt or a solvate thereof.

2. A process according to claim 1, wherein in compounds of formula (I) W represents a chiral auxiliary.

3. A process according to claim 1 for the preparation of a compound of formula (Ia),

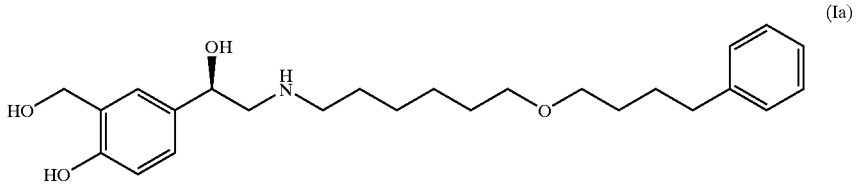

(Ia)

(R-salmeterol), or a salt or a solvate thereof, which comprises:

a) treating a compound of formula (IIa),

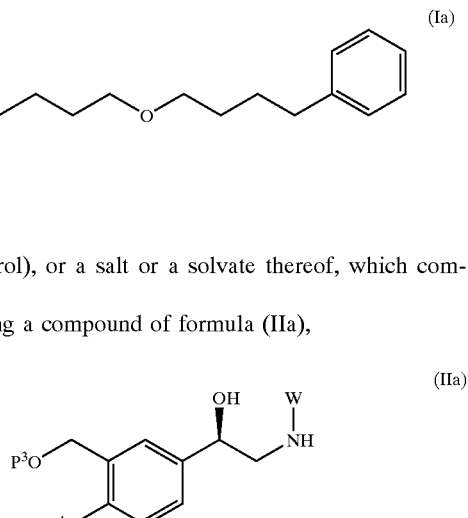

(IIa)

or a salt or a solvate thereof, wherein W is a chiral auxiliary and $P^3$ arid $P^4$ are each independently chosen from a protecting group, with a compound of formula (III), as defined in claim 1 to form a resulting product, and b) treating the resulting product with a reducing agent to form the compound of formula (Ia), or a salt or a solvate thereof.

4. A process according to claim 1 for the preparation of S-salmeterol using the appropriate enantiomer of a compound of formula (II).

5. A process according to claim 1 wherein the salt is xinafoate.

6. A process as claimed in claim 1 wherein W represents a moiety of the formula (Y)

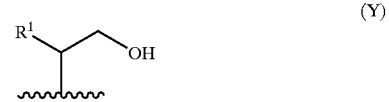

(Y)

or a single enantiomer thereof, wherein $R^1$ represents phenyl, iso-propyl or sec butyl.

7. A process as claimed in claim 1 wherein W represents a moiety of the formula (Ya)

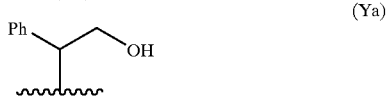

(Ya)

or a single enantiomer thereof.

8. A process as claimed in claim 1 wherein $P^3$ and $P^4$ together with the oxygens to which they are attached represent acetonide.

9. A process as claimed in claim 1 further comprising removing at least one substitute selected from protecting group $P^1$, protecting group $P^2$, chiral auxiliary W, and combinations thereof to give salmeterol or a single enantiomer thereof.

10. A process according to claim 9 wherein Pearlman's catalyst is used to remove the chiral auxiliary W.

* * * * *